United States Patent [19]
Suzuki et al.

[11] Patent Number: 4,892,522
[45] Date of Patent: Jan. 9, 1990

[54] DEVICE FOR PREVENTING INJURY WHEN CAPPING INJECTOR NEEDLE AFTER USE

[75] Inventors: Tsuyoshi Suzuki, Tokyo; Shoji Kudoh, Noda, both of Japan

[73] Assignee: Seirin Kasei Co., Ltd., Shimizu, Japan

[21] Appl. No.: 206,365

[22] Filed: Jun. 14, 1988

[30] Foreign Application Priority Data

Jun. 17, 1987 [JP] Japan .............. 62-93108[U]
Jan. 13, 1988 [JP] Japan .............. 63-1986[U]
Jan. 13, 1988 [JP] Japan .............. 63-1987[U]

[51] Int. Cl.$^4$ ............................................. A61M 5/32
[52] U.S. Cl. ................................. 604/192; 604/263
[58] Field of Search .................. 604/192, 187, 263

[56] References Cited

U.S. PATENT DOCUMENTS 4,485,918 12/1984 Mayer ..................... 604/263 X
4,742,910 5/1988 Staebler ................... 604/192 X
4,781,697 11/1988 Slaughter ................. 604/192

FOREIGN PATENT DOCUMENTS 0192453 8/1986 European Pat. Off. ............ 604/192
59-19146 5/1984 Japan.
59-16648 6/1984 Japan.

Primary Examiner—John D. Yasko
Attorney, Agent, or Firm—Finnegan, Henderson, Farabow, Garrett & Dunner

[57] ABSTRACT

A device for preventing injury to the fingers of a person holding a cap into which an injector needle is inserted after use. The device is formed as a plate shaped member having a plane substantially transverse to the axis of the tube and having an area large enough to stop movement of the needle is not properly inserted into the cap when capping the injector. The plate member is provided with a thin-walled portion having a central opening and/or axial slits having inner edges which are elastically flexed and thus maintan a tight grip on the outer surface of the cap. Accordingly, the plate member is firmly fixed to the cap, and prevents injury to the fingers of a person holding the cap, by the needle, of the injector.

10 Claims, 3 Drawing Sheets

DEVICE FOR PREVENTING INJURY WHEN CAPPING INJECTOR NEEDLE AFTER USE

BACKGROUND OF THE INVENTION

1. Field of the Invention

The present invention relates to a device for preventing injury when capping the needle after the needle has been used. p 2. Description of Related Arts Personel such as doctors and nurses engaged into the medical treatment of patients suffering from a contagious disease are continually exposed to the risk of catching such a contagious disease. The most frequent causes of such contagion are accidents occurring while recapping an injector needle after use. Namely, when an injector needle is inserted into a cap (also called a protector) after use for subsequent treatment, it is difficult to correctly insert the tip end of the injector into the opening of the cap held by the operator, and if the needle misses the opening of the cap, it can penetrate the fingers of the person holding the cap. Such accidents can also occur during subsequent treatment of the needle, for example, the cleaning thereof, while the needle is not capped.

To prevent such injuries caused by an injector needle, a cap for an injector needle has been proposed which is formed as a tube having a outwardly tapered open end forming a flange, to thereby make it easier to insert the injector needle into the cap while holding it and to prevent injury to the fingers. See Japanese Un-examined Utility Model Publication No. 59-16648 and Japanese Un-examined Utility Model Publication No. 59-19146.

This type of cap has a disadvantage in that, in general a large number of injectors must be each tilted with a cap after sterilizing action to prevent contamination by bacteria before subsequent usage, and thereafter packed together as compactly as possible. The above mentioned flanged cap however, does not allow such a compact packing due to the size of the flange provided thereon.

Furthermore, caps having various dimension are required due to the variety of sizes of the needles, and thus a cap having a certain dimension can not be commonly used for different size needles. Accordingly, there is a demand for a new type of flanged cap having a wider usage.

SUMMARY OF THE INVENTION

An object of the present invention is to provide a device for preventing injuries caused by an injection needle, which device is separate from and can be adapted for use with different types of injector caps.

Another object of the present invention is to provide the device which can be commonly used with caps having various diameters. According to one aspect of the present invention, a device is provided for use together with a tubular cap for an injector, for preventing injuries by an injector needle, comprising a plate shaped member made of a synthetic resin material and having a plane extending substantially transversely to the axis of the tubular cap. The plate member comprising an outer peripheral portion having a large axial thickness for providing the plate shaped member with a desired strength and an inner portion integral with the outer portion and having a thickness smaller than the thickness of the outer peripheral portion, said inner portion having a means for bringing inner edge portions thereof into contact with and gripping the outer surface of a cap member, when the cap is inserted into the plate-shape member, by an elastic flexure of the inner edge portions.

According to another aspect of the present invention, a cap assembly for an injector is provided which comprises:

an axially extending tubular cap having a first narrow closed end and a second wide and open end axially remote from the first end, and;

a plate shaped member, into which to the tubular cap member is inserted made of a synthetic resin material and having a plane extending substantially transversely to the axis of the tubular cap, the plate member comprising an outer peripheral portion having a large axial thickness for providing the plate shaped member with a desired strength and an inner portion integral with the outer portion and having a thickness smaller than the thickness of the outer peripheral portion, the inner portion having a means for bringing an inner edge portion thereof into contact with and gripping the outer surface of the cap member, when the cap is inserted into the plate shaped member, by an elastic flexure of the inner edge portions.

DESCRIPTION OF THE PREFERRED EMBODIMENTS

Figure 1:
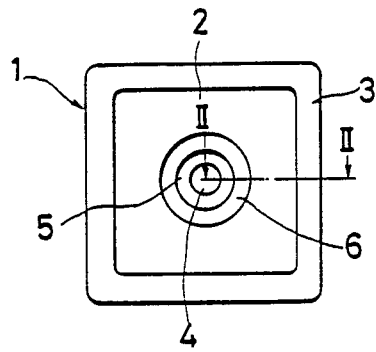
FIG. 1 is a plane view of the plate member according to a first embodiment of the present invention.

The preferred embodiments of the present invention will be explained with reference to the attached drawing. In FIG. 1, reference numeral 1 denotes a plate-shaped adapter made from a synthetic resin material such as polypropylene, polyethylene, or polyvinyl chloride, or an elastomer having a stiffness such that a tip end of an injector needle can not easily penetrate therethrough and an elasticity sufficient to allow a flexing thereof to enable easy insertion thereof onto a cap. In particular, polypropylene is preferable, and if polyethylene is used, it must have a high density.

The plate shaped member 1 is generally formed into a square shape, each side thereof having a length of 25 mm. The plate member 1 has a main part comprising a thick wall portion 2 having a thickness of 0.8 mm, and a frame portion 3 having thickness of 1.2 mm peripherally surrounding the main portion 2. The plate member 1 is provided at the center thereof, with a circular opening 4 for introduction portion of a cap. The location of the opening 4 is not limited to the center portion of the plate member 1, and it can be located at any position convenient for the insertion of a cap and so long as protection is provided for the fingers of the person holding the cap. Further, the opening 4 can be a shape other than circular as long as a firm grip on the cap is provided thereby.

Figure 2A:
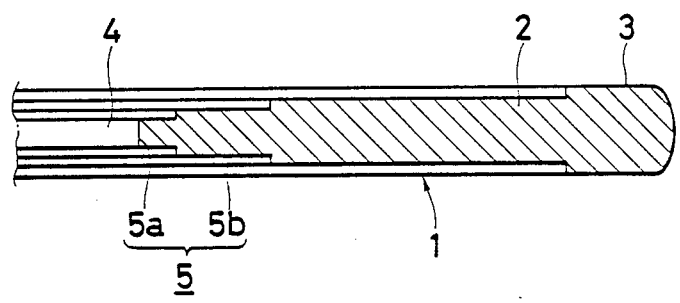
FIG. 2A is an enlarged partial cross sectional view of the plate member in FIG. 1, taken along line II—II in FIG. 1.

As shown in FIG. 2A, the plate member 1 has a stepped-shaped thin-walled portion 5 located around the opening 4. The stepped portion 5 comprises a first or inner thin-wall portion 5a and a second or outer thin-wall portion 5b. The inner diameter as well as the thickness are increased from the center of the opening 4 in the order of the first thin-walled portion 5a and the second thin-walled portion 5b. In this embodiment first and the second thin-walled portions 5a and 5b constitute a flexible thin-walled portion.

The step-like shape of the plate member 1 is such that the thickness of the first thin-walled portion 5a is 1/5 to ½, preferably ⅛ to ½, of the thickness of the second thin-walled portion 5b. Furthermore, the thickness of the outer second thin walled portion 5b is greater than that of the first thin-walled portion 5a and thick-walled portion 3. The inner diameter of the opening 4 is preferably slightly smaller than the outer diameter of a generally used cap. This outer diameter of the cap is at a position near the open end thereof. For example, the opening 4 has an inner diameter of about 6.4 mm, the first thin-walled portion has an inner diameter of about 10.0 mm, and the second thin-walled portion has an outer diameter of about 10.0 mm. Of course, these dimensions can be suitably modified in accordance with the particular diameter of the cap for an injector, but the above-mentioned dimensions are sufficient for usually used cap.

The first thin-walled portion 5 has a greater flexibility for accommodating various sized outer diameters of caps, and thus the portion 5 can be easily flexed to realize a sealing contact with the outer surface of the cap.

Figure 2B:
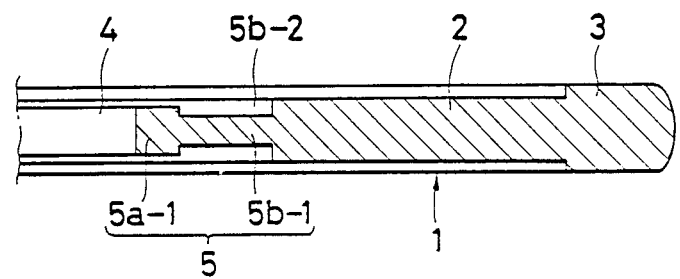
FIG. 2B is an enlarged partial cross sectional view of a modified plate member.

In the above mentioned embodiment, the flexible portion 5 is constructed in two steps, comprised of the first thin-walled portion 5a and the second thin-walled portion 5b, but one or more additional stepped portions may be provided. Alternatively, the thickness of the portion 5 can be gradually decreased or tapered from the outside to the inside thereof. Furthermore, as shown in FIG. 2B, the second thin-walled portion 5b-1 may be thinner than the first thin-walled portion 5a-1. The provision of the recess 5b-2 gives the first thin-walled portion 5a-1 a greater flexibility. As shown in the drawings, each of the portions around the opening 4 has the same thickness, but the thickness of each portion can be suitably varied. Furthermore, a construction is also possible wherein thin-walled portions and the thick-walled portions are alternately arranged.

The thin-walled portion 5 allows the plate member 1 to accommodate injector caps having various outer diameters, because the portion 5 is made of a flexible resin material and has a small thickness.

Also the outer surface of the thick-walled portion 2 can be embossed, i.e., given a satin-embossed finish, to prevent the tip end of the needle from slipping on the plate 1 during use.

The outer thick-walled frame portion 3 strengthens the plate member 1 as a whole.

The operation of this first embodiment of the device for preventing an injury by an injector, according to the present invention, is as follows.

Figure 3:
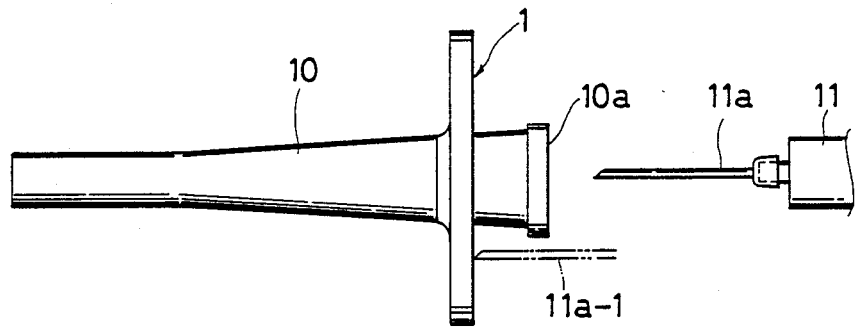
FIG. 3 is a side view illustrating the insertion of the injector into a cap held by the plate member according to the present invention.

As shown in FIG. 3, the plate member 1 is pushed onto the cap 10 from the narrowed bottom end thereof until it reaches a position near the open end 10a of the cap 10. The tip end (needle) 11a of the injector 11, which may be a source of infection by bacteria is, introduced into the cap 10 via the open end 10a, while holding the end of the cap remote from the open end 10a. If the needle 11a is properly inserted into the cap, no any problem arises but occasionally, the needle may miss the opening 10a, since the inner diameter of the cap 10 is relatively small. In this situation, the fingers of the person holding the cap 10 are not pierced by the needle, because the needle comes into contact with the plate member 1, and thus the needle cannot reach the fingers.

Figure 4:
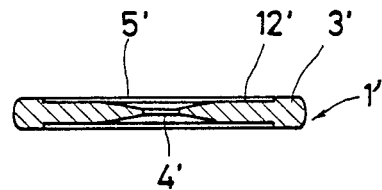
FIG. 4 is a cross sectional view of another embodiment according to the present invention.

In a modification shown in FIG. 4, a thin-walled portion 5' is provided which is tapered inwardly toward the central opening 4'. The thin-walled portion 5' is connected, via a thick-walled portion 2', to a flange portion 3' forming the periphery of the plate member 1'. This modification can also provides a better grip on the cap when the cap has noticeable variation of the outer diameter thereof.

Figure 5:
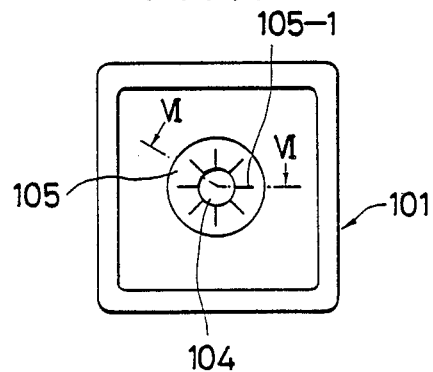
FIG. 5 is a plane view of another embodiment of the plate member according to the present invention.
Figure 6A:
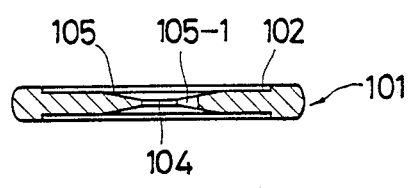
FIG. 6A is a cross sectional view of the plate member in FIG. 5, taken along the line VI—VI in FIG. 5.

In an embodiment of the present invention shown in FIGS. 5 and 6A, a plate 101 has a tapered thin-walled portion 105, as in FIG. 4, is provided, which portion 105 further includes a plurality of equiangularly spaced slits 105-1, each of which extends radially and outwardly from the inner edge of a central opening 104 thereof within the tapered thin-walled portion 105. In this embodiment this construction of slits 105-1 combined with the tapered thin-walled portion 105 provides a high flexibility when the cap is introduced therein. Also the above slit construction can be suitably combined with the step like thin-walled construction of the previously described embodiment.

Figure 6B:
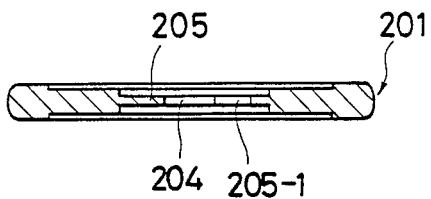
FIG. 6B is a cross-sectional view of another embodiment of the plate member according to the present invention.

FIG. 6B shows a modification of the plate 201 wherein a thin-walled portion 205 has a uniform thickness. The portion 205 is provided with slits 205-1 similar to the slits 105-1 in FIG. 6A.

The shape of the plate member is not limited to the square shape as illustrated, and another shape such as a polygonal, circular or non-circular shape may be employed. If the circular shape is employed, a means may be provided to prevent the injector from rolling when laid down.

In the embodiment in FIGS. 6A and 6B, the slits 105-1 or 205-1 provide an increase flexibility, to allow an easier introduction of the cap into the plate member 101 or 201. The number, location and length of the slits are determined so that the portion 105 or 205 around the opening 104 or 204 is effectively flexed to realize a tight contact with the outer surface of the cap. If the thin-walled portion 105 or 205 and the slits 105-1 and 205-1 are combined, a high degree of flexibility is easily obtained.

Figure 7:
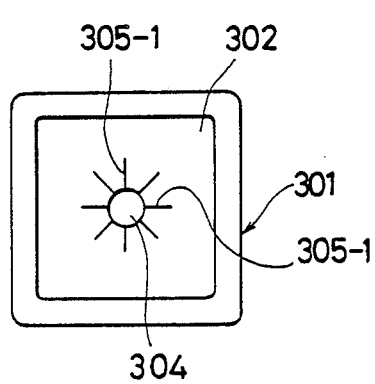
FIG. 7 is a plane view of another embodiment of the plate member according to the present invention.
Figure 8:
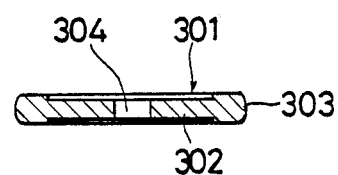
FIG. 8 is a cross sectional view of the plate member in FIG. 7.

Another embodiment is shown in FIGS. 7 and 8, wherein the thin-walled portion of the previously explained embodiments is not provided, and therefore, the thick-walled portion 302 extends to the central opening 304 at which the cap is introduced. A plurality of angularly spaced slits 305-1 extend outwardly from the inner periphery of the opening, and in this case, similar to the embodiment in FIGS. 5 and 6A, the number, location and length of the slits 305-1 are determined so that the portion 302 around the opening 304 is effectively flexed to realize a tight contact with the outer surface of the cap.

Figure 9:
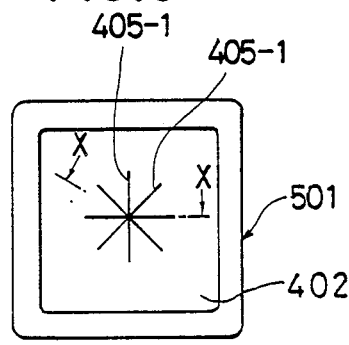
FIG. 9 is a plane view of another embodiment of the plate member according to the present invention.
Figure 10:
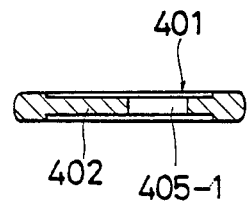
FIG. 10 is a cross sectional view of the plate member in FIG. 9, taken along the line X—X in FIG. 9.

In another embodiment in FIGS. 9 and 10, a central opening is not provided, but to allow the introduction of the cap into the plate member 501, a plurality of radial slits 405-1 extend from the center axis of the plate 501 and inner ends of the each of the slits 405-1 are opened away from each other, to define corresponding edges separate from each other. When the cap is inserted into the plate member 501, the part of the portion 402 provided with slits 405-1 is flexed, and these inner edges come into tight contact with the outer surface of the cap. In this embodiment, the number location and length of the slits 405-1 are also determined so that the portion 402 in the center of the plate member 501 is effectively flexed to realize a tight contact with the outer surface of the cap.

According to the present invention, by pushing the plate member on to the cap of an injector, the fingers of the person holding the cap cannot be pierced by the needle due to the plate member, and the needle cannot move further even when moved during an attempt to insert same in the opening of the cap.

The cap combined with the plate member according to the present invention can be stored under very compact conditions before use, even if the injectors are capped, since the caps are not flanged. Therefore, the present invention is very advantageous from the view point of the sterilization of a large amount of injectors and a prevention of contamination by bacteria thereof during storage before use.

Furthermore, the provision of slits on the plate members is very convenient in that a common plate can be utilized for various diameters or shapes of caps, which effect can not be obtained by the conventional type.

Also, as the present invention is formed into a plate shape made from a synthetic resin material, the name of a patient or the dosage drug can be easily written thereon. Furthermore, the ward, drug, and number of shots can be easily identified by applying various colors to the plate members.

Furthermore, the provision of a stepped or tapered thin-walled portion provides the plate member with a high flexibility, and the provision of a polygonal shape for the plate member will prevent the cap from rolling away when laid down.

While the present invention is described with reference to the attached drawing, many modifications and changes can be made by those skilled in this art without departing from the scope and spirit of the invention.

We claim:

1. A device for use with a tubular cap for an injection needle, comprising a plate shaped member made of a synthetic resin material and having a plane when assembled on the cap that extends substantially transverse to the axis of the tubular cap, said plate member comprising an outer peripheral wall portion having an axial thickness that provides the plate shaped member with the required strength and an inner wall portion integral with the outer portion and having a thickness smaller than the thickness of the outer peripheral portion, said inner wall portion having an inner edge defining an opening having an inner diameter which is smaller than the outer diameter of the cap near the end where the needle is to be inserted, a first thin-walled portion and a second thin-walled portion having a thickness larger than that of the first thin-walled portion, the inner wall portion of the plate shaped member elastically flexing as the cap is inserted through the opening in the plate-shaped member with the inner edge of the opening gripping the outer surface of the cap to hold the plate in place.

2. The device of claim 1, wherein the first thin-walled portion of the inner wall portion surrounds the opening and the second thin-walled portion is integral with and is located between the first thin-walled portion and the outer peripheral portion.

3. The device of claim 1, wherein the second thin-walled portion of the inner wall portion surrounds the opening and the first thin-walled portion is integral with and is located between said second thin-walled portion and the outer peripheral portion.

4. A device for use with a tubular cap for an injection needle, comprising a plate shaped member made of a synthetic resin material and having a plane when assembled on the cap that extends substantially transverse to the axis of the tubular cap, said plate member comprising an outer peripheral wall portion having an axial thickness that provides the plate shaped member with the required strength and an inner wall portion integral with the outer portion and having a thickness smaller than the thickness of the outer peripheral portion, said inner wall portion having an inner edge defining an opening having an inner diameter which is smaller than the outer diameter of the cap near the end where the needle is to be inserted and tapering in thickness from the opening outwardly toward the outer peripheral wall portion, the inner wall portion of the plate-shaped member elastically flexing as the cap is inserted through the opening in the plate-shaped member with the inner edge of the opening gripping the outer surface of the cap to hold the plate in place.

5. The device of claim 4, wherein said inner wall portion has a plurality of angularly spaced slits, each of said slits extending radially outwardly from the opening to provide a plurality of inner edges defining the opening, which edges are elastically flexed when said tubular cap is inserted through the opening in the plate member.

6. A cap assembly for an injection needle, comprising:
an axially extending tubular cap having a first narrow closed end and a second wide open end and axially remote from the first end, and;
a plate shaped member, through which the tubular cap is inserted, made of a synthetic resin material and having a plane extending substantially transverse to the axis of the tubular cap, said plate member comprising an outer peripheral wall portion having an axial thickness that provides the plate shaped member with the required strength and an inner wall portion integral with the outer portion and having a thickness smaller than the thickness of the outer peripheral portion, said inner wall portion having an inner edge defining an opening having an inner diameter which is smaller than the outer diameter of the cap near its open end, a first thin-walled portion and a second thin-walled portion having a thickness larger than that of the first thin-walled portion, the inner wall portion of the plate shaped member elastically flexing as the cap is inserted through the opening in the plate-shaped member with the inner edge of the opening gripping the outer surface of the cap to hold the plate in place.

7. The cap assembly of claim 6, wherein the first thin-walled portion of the inner wall portion surrounds the opening and the second thin-walled portion is integral with and is located between the first thin-walled portion and the outer peripheral portion.

8. The cap assembly of claim 6, wherein the second thin-walled portion of the inner wall portion surrounds the opening and the first thin-walled portion is integral with and is located between said second thin-walled portion and the outer peripheral portion.

9. A cap assembly for an injection needle, comprising:
an axially extending tubular cap having a first narrow closed end and a second wide open end axially remote from the first end, and;
a plate-shaped member, through which the tubular cap is inserted, made of a synthetic resin material and having a plane extending substantially transverse to the axis of the tubular cap, said plate member comprising an outer peripheral wall portion having an axial thickness that provides the plate shaped member with the required strength and an inner wall portion integral with the outer portion and having a thickness smaller than the thickness of the outer peripheral portion, said inner wall portion having an inner edge defining an opening having an inner diameter which is smaller than the outer diameter of the cap near its open end and tapering in thickness from the opening outwardly toward the outer peripheral wall, the inner wall portion of the plate shaped member elastically flexing as the cap is inserted through the opening in the plate-shaped member with the inner edge of the opening gripping the outer surface of the cap to hold the plate in place.

10. The cap assembly of claim 9, wherein said inner wall portion has a plurality of angularly shaped slits, each of said slits extending radially outwardly from the opening to provide a plurality of inner edges defining the opening, which edges are elastically flexed when said tubular cap is inserted through the opening in the plate member.

* * * * *